(12) United States Patent
Laor et al.

(10) Patent No.: US 8,390,825 B2
(45) Date of Patent: Mar. 5, 2013

(54) DOUBLE SEAM MEASUREMENT SYSTEM

(76) Inventors: Benny Laor, Kiryat Bialik (IL); Nadav Leshem, Mizpe Lavon (IL)

( * ) Notice: Subject to any disclaimer, the term of this patent is extended or adjusted under 35 U.S.C. 154(b) by 168 days.

(21) Appl. No.: 13/087,811

(22) Filed: Apr. 15, 2011

(65) Prior Publication Data
US 2012/0262734 A1 Oct. 18, 2012

(51) Int. Cl.
*G01B 11/14* (2006.01)
*G01N 21/00* (2006.01)
(52) U.S. Cl. ..................... 356/625; 356/240.1
(58) Field of Classification Search ............... 356/240.1, 356/625, 635–637
See application file for complete search history.

(56) References Cited

U.S. PATENT DOCUMENTS 5,104,226 A * 4/1992 Eble et al. ..................... 356/391
5,386,293 A * 1/1995 Barnard et al. ............... 356/397

\* cited by examiner

*Primary Examiner* — Michael P Stafira
(74) *Attorney, Agent, or Firm* — Wiliam H. Dippert; Eckert Seamans Cherin & Mellott, LLC

(57) ABSTRACT

A system for measurement of a can seam of a can comprising a an end panel, the end panel comprising the seam, the seam comprising a circumference, a seam top, a seam bottom, a seam chuck wall part and an opposite seam wall essentially opposite the seam chuck wall part, the system comprising: a table comprising a table top; a rocker comprising an inner pin and an outer pin essentially parallel to each other, the rocker configured to allow, when the end panel of the can is facing the table top, slight pressure of the outer pin on the opposite wall forcing the chuck wall part on the inner pin, and/or slight pressure of the inner pin on the chuck wall part forcing the opposite wall on the outer pin, causing rocking movement of the pins, that settles the inner pin flush with the chuck wall part, and/or the outer pin flush with the opposite wall, respectively, such that the inner pin and outer pin are disposed at chuck wall angle; means for rotating the can, allowing the inner pin to settle flush with the chuck wall part, and the outer pin to settle on a peak point on the opposite wall, at measurement points on the circumference of the seam, and measuring means configured to be able to measure a gap between the inner pin and the outer pin at the measurement points.

30 Claims, 13 Drawing Sheets

DOUBLE SEAM MEASUREMENT SYSTEM

FIELD OF THE INVENTION

The present invention relates to double seam measurement.

BACKGROUND OF THE INVENTION

Double seams have been in use by can fillers and can makers in order to ensure a high quality seal inside a metal container, which helps provide longer durability of their contents and a higher degree of separation from environmental hazards and contamination.

The double seam is typically performed inside a seamer, typically by having a cover locked into a chuck, and then the cover and a can flange are folded twice into a double seam.

In order for the seal to remain secure, the double seam closure must be maintained all around the can. This is of critical importance, so anyone closing seams (can fillers as well as can makers) and some recipients of enclosures, which contain closed seams must make routine checks to ensure these seams are sealed properly.

The FDA presently requires at least one test set to be performed at intervals of once every 4 hours. These tests require taking a complete set of cans from a seaming line—at least one sample per seamer head; Seamers can contain between 1 and 24 individual heads) from a production line, at different stages of the double seam production.

The tests include either or both non-destructive tests (NDT's) and destructive (teardown or sectioning) tests.

Destructive tests typically involve a teardown procedure, which uses a can stripper to remove the cover-hook from the can and allows for visual inspection. Additional destructive tests include cutting through the seam at 1 to 4 sections at regular intervals around the can, and inspecting the image of the cut cross section of the seam. These types of destructive tests provide valuable information regarding that particular measurement section, such as overlap, body and cover-hooks, body and cover hook butting, free space as well as seam length and thickness.

Additional issues that can occur are various issues like false seam (where the closure process misses or slips and the seam is actually open in some areas), vee, droops, asymmetrical closure (the overlap hangs to one side), small overlap, and large free-space (the seam is too "open"). Other cosmetic issues, such as sharp seams can be cosmetic but do not interfere with the closure's seal.

However, the cutting itself can warp or extend the cut material such that the measurements contain artifacts such as burrs. Moreover, only a few cuts may be made per can without losing can integrity.

Non-destructive tests may include pressure testing (typical strain gauges as part of the seaming process), X-ray measurements, and external measurements, such as using a caliper, or specially designed gauges—the latter typically serving for measurement of countersink, seam thickness (also known as seam width) and seam length (also known as seam height).

One double seam measurement system is described in U.S. Pat. No. 4,600,347 to Continental Can Company, Inc. (US), in which part of a cam of a double seaming apparatus is deformable. Strain gauges monitor the deformation of this part of the cam track and the signal from the gauges is processed to identify abnormal conditions together with details of the specific force, relevant machine and date/time of each abnormal condition.

U.S. Pat. No. 7,736,112 to Crown Packaging Technology, Inc. (US) describes another double seam monitor device for measuring the strain/force applied by a lifter cam so as to provide information interpreted to indicate seam quality, gross seam defects and seaming machine condition. The apparatus includes: a lifter mechanism for lifting the can body; seaming tooling, and a device for measuring the strain of and/or force applied to the lifter mechanism by the lifter cam.

The CSG-2073 gauge by CMC to CMC Kuhnke GMBH (DE) is described by the manufacturer as a semi-automatic gauge equipped with double seam thickness and optionally double seam height measurement systems, in which after a can has been placed into position, an LVDT (Linear Variable Differential Transformer) gauge measures at up to 50 points (around the diameter of the can).

WO2010048914 to CMC Kuhnke GMBH (DE) describes a positioning device for analyzing a double seam cross-section using X-rays, including an X-ray source, having a first stop associated therewith for a can to be analyzed in the region of the outlet opening for the X-rays, and detectors for receiving the X-rays. The can to be analyzed is clamped relative to the X-ray source by way of at least three stops disposed offset from each other, wherein the positions of two of said stops can be actively varied in order to perform an adjustment.

However, X-ray systems measure at only a few points around the can, and pressure systems on the seamer can miss even obvious issues because of their technology (e.g., false seams, for example when the body and cover edges are not folded into each other).

A very serious disadvantage of many double seam tests is that a very small section of the double seam is sampled around the can. This works as long as the seam is consistent around the circumference of the can. However, when there are local defects in particular areas, this method will most likely miss them, which means that the tests do not ensure that the can being tested is, in fact, sealed—many tests would have to be conducted until the problem is identified as consistent. Another alternative is to increase the testing rate (from the mandated once per 4 hours to round the clock testing, or even real time testing), but such methods will still test one or more sections of the can and not the entire circumference of the can itself. Local defects include for example composition buildup, seam skids, bumps, dimples, wrinkles Bad seamer bearings, cracked tooling and seamer setup issues (such as loose setup, loose shafts or shanks) can cause issues that may only be apparent by inspecting the seam all around the can. Not just peak points outside the specifications are of issue, but also range issues that can identify that the seaming process is oscillating.

Considering that beverage cans can reach as much as 4000 cpm in production environments, as well as the trend to reduce can end diameters and material thicknesses, the seaming process is now far more prone to manufacture errors that can be missed. Moreover, control limits have been reduced accordingly, as part of the initiative to reduce wall thicknesses and narrowing of can necks.

Even with increased test rates, a problem can nevertheless be missed due to small localized flaws that would result in many cans during production simply being bad. With Just in Time production, the distance from manufacturing to distribution is shortened. If a local flaw results in cans going out of the control limits even at a small area around the seam, this issue can be discovered many hours after cans were being produced; Since cans are shipped out almost immediately after being production and testing, this could result in massive recalls.

It should be noted that cans with micro-leaks or that do not have a tight enough seal can expose the consumer not just to eating spoilt or degraded food, but can also expose the contents of the can to harmful industrial chemicals, such as anti-fungal sprays and fluids, that are used near where cans are stored. Cans that are exposed to such chemicals without being completely sealed could result in food poisoning.

Most if not all commercially available seam measurement systems, such as various calipers applied to the seam walls, e.g. feeler gauges, are not capable of accurately positioning the system according to the chuck wall angle. In some systems a manual and/or other adjustment is made to adjust the system orientation according to the chuck wall angle at each point of measurement or even set to a fixed value. Apparently, the angle does vary somewhat around the seam of a can (particularly if there is a defect in the chuck, in the bearing, bushing or orientation of the can), and from can to can in a batch. It is very difficult and lengthy to make a correct orientation, and incorrect measurements in this respect, are both inaccurate and imprecise. Moreover, the delicate and flexible nature of double seams, in particular in beverage cans, can further result in different operators obtaining completely different results for the same measurement point. Some other systems allow fixating a measured can such that the can is at a presumably constant angle (or modifiable angle, that is changed manually) relative to a reference area on the measuring system. Nevertheless, such systems also are inaccurate and imprecise.

The invention aims to provide improved measurement of double seams. The objective is to reduce the number of missed local problems by fully inspecting each can.

SUMMARY OF THE INVENTION

According to one aspect, a system is provided for measurement of a can seam of a can comprising a an end panel, the end panel comprising the seam, the seam comprising a circumference, a seam top, a seam bottom, a seam chuck wall part and an opposite seam wall essentially opposite the seam chuck wall part, the system comprising:
  a table comprising a table top;
  a rocker comprising an inner pin and an outer pin essentially parallel to each other, the rocker configured to allow, when the end panel of the can is facing the table top, slight pressure of the outer pin on the opposite wall forcing the chuck wall part on the inner pin, and/or slight pressure of the inner pin on the chuck wall part forcing the opposite wall on the outer pin, causing rocking movement of the pins, that settles the inner pin flush with the chuck wall part, and/or the outer pin flush with the opposite wall, respectively, such that the inner pin and outer pin are disposed at chuck wall angle; means for rotating the can, allowing the inner pin to settle flush with the chuck wall part, and the outer pin to settle on a peak point on the opposite wall, at measurement points on the circumference of the seam, and measuring means configured to be able to measure a gap between the inner pin and the outer pin at the measurement points.

According to another aspect, a system is provided for measurement of a can seam, the seam comprising a circumference, a seam top, a seam bottom, a seam chuck wall part and an opposite seam wall essentially opposite the seam chuck wall part, the system comprising:
  a length plate having an edge;
  positioning means configured to allow positioning a can for measurement of the distance between the seam top and seam bottom;
  means for moving the length plate until the length plate edge resides on the seam top,
  and measurement means configured to allow measuring a plate distance between a point on the length plate and a fixed reference point,
  the distance representing a seam distance between the seam top and the seam bottom.

According to a third aspect, a system is provided for measurement of a can seam, the seam comprising a circumference, a seam top, a seam bottom, a seam chuck wall part and an opposite seam wall essentially opposite the seam chuck wall part, the system comprising:
  a length plate comprising an edge;
  means for moving the length plate until the length plate edge resides on the seam top; means configured to allow measuring a plate distance between a point on the length plate and a fixed reference point, the distance representing a seam distance between the seam top and the seam bottom;
  a rocker comprising an inner pin and an outer pin essentially parallel to each other, the rocker configured to allow applying slight pressure of the inner pin on the chuck wall part and slight pressure of the outer pin on the opposite wall, and rocking movement of the outer and inner pin relative to the seam, thereby forcing the inner pin to settle flush with the chuck wall part, and the outer pin to settle on a peak point on the side wall;
  means for rotating the can, allowing the inner pin to settle flush with the chuck wall part, the outer pin to settle on a peak point on the side wall at measurement points on the circumference of the seam, and the reference point to be at essentially constant height during the rotation of the can and measuring means configured to allow measuring both a plate distance between a point on the length plate and a reference point, and a distance representing a seam distance between the seam top and the seam bottom.

In some systems with a rocker, least one pin may be configured to rotate with the can.

In some of the systems with a length plate, the length plate is preferably circular, and may be configured to rotate with the can.

In some of the systems with a length plate, the system may further comprise:
  means for rotating the can, allowing the reference point to be at constant height during the rotation of the can.

In some of the systems with a length plate, the length plate is preferably circular, and may be configured to rotate with the can.

In some of the systems with a length plate, the system may further comprise:
  means for rotating the can, allowing the reference point to be at constant height during the rotation of the can.

In some of the systems with a length plate, the length plate comprises a tooth, essentially parallel to the edge, wherein a point on the tooth is selectable for measuring a distance between the tooth and the reference point representing a distance between the seam top and the seam bottom.

In some of the systems with a rocker, measurement means comprises an optic setup, the optic setup comprising a light source capable of emitting light and a sensor of the light, wherein the sensor is positioned to receive light partially blocked by the pins to detect a silhouette of the pins, such that the silhouette comprises a gap between the pins representing a distance between the seam chuck wall part and the opposite seam wall.

The settled pins are for example positioned relative to the seam such that parts of each of the pins extend beyond the seam, such that the gap is devoid of the seam.

In some of the systems with a length plate, measurement means may comprise an optic setup, the optic setup comprising a light source capable of emitting light and a sensor of the light, wherein the sensor is positioned to receive light partially blocked by the length plate to detect a silhouette of the length plate, such that the silhouette comprises a gap between the length plate and the reference point.

The rocker may swivel on a stationary part, the stationary part comprising an aperture allowing light from the light source to be aimed throughout the stationary part at the pins and length plate.

The aperture may comprise a lens for focusing or defocusing the light passing through the aperture.

The system may further comprise signal processing means configured to process signals received by the sensor into data, means for storing the data and means for presenting the data.

In some of the systems with a length plate, the can comprises a neck, wherein the length plate substantially conforms with at least part of the neck, thereby allowing the plate to be stably held against the can during rotation of the can.

In some of the systems with a rocker, the table top is a sliding table top.

The length plate may comprise at least one tooth, wherein the point on the length plate is a point on a tooth, the point is known before the measuring.

In some of the systems with a rocker, at least one rotating pin may be covered by high friction material ensuring traction with the can during the rotation.

BRIEF DESCRIPTION OF THE FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawings making apparent to those skilled in the art how the several forms of the invention may be embodied in practice.

In the accompanying drawings:

FIG. 1a shows a basic seamer design;

FIG. 1b shows a top view of an end of a can;

FIG. 2 shows a side section of a loose first operation;

FIG. 3 shows a side section of tight first operation;

FIG. 4 shows a side section of a first defect double seam;

FIG. 5 shows a side section of a another defect double seam;

FIG. 6 shows a side section of a third defect double seam;

Figure 7:
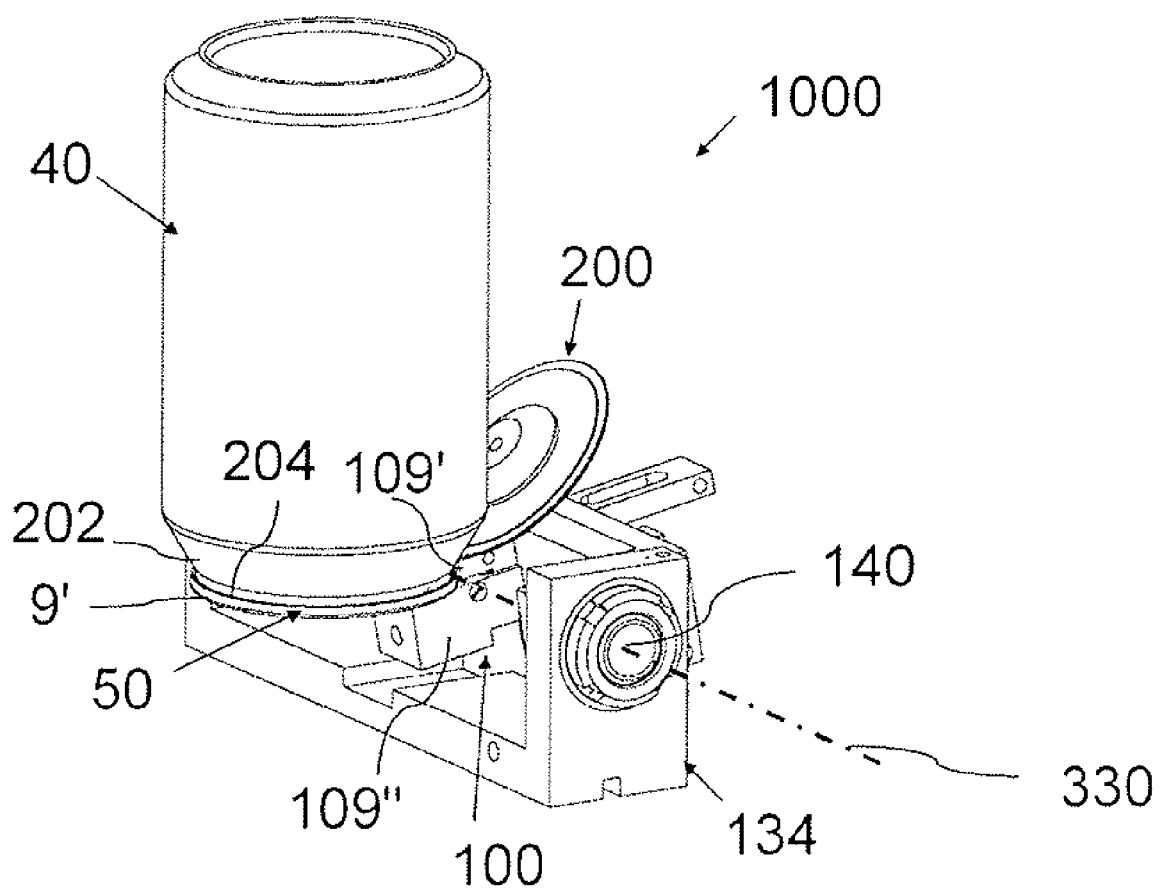
Figure 8:
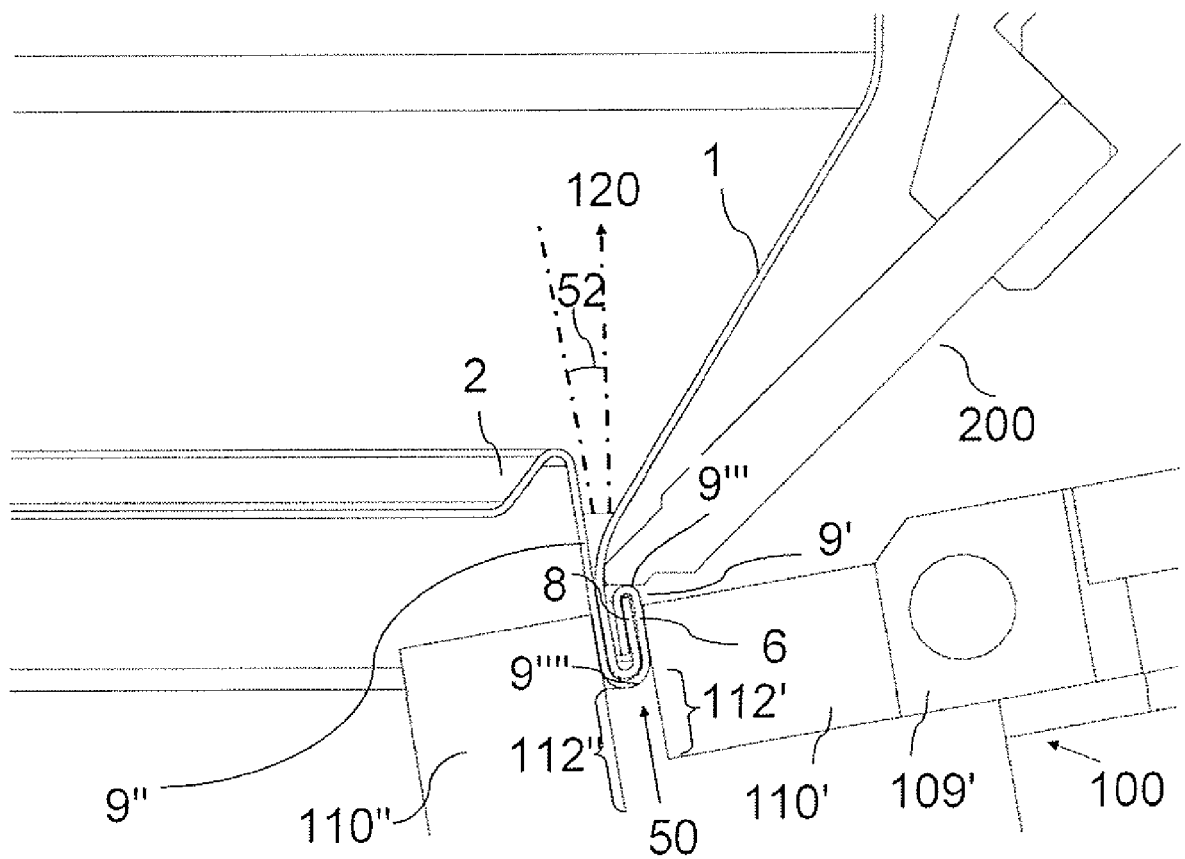
Figure 9:
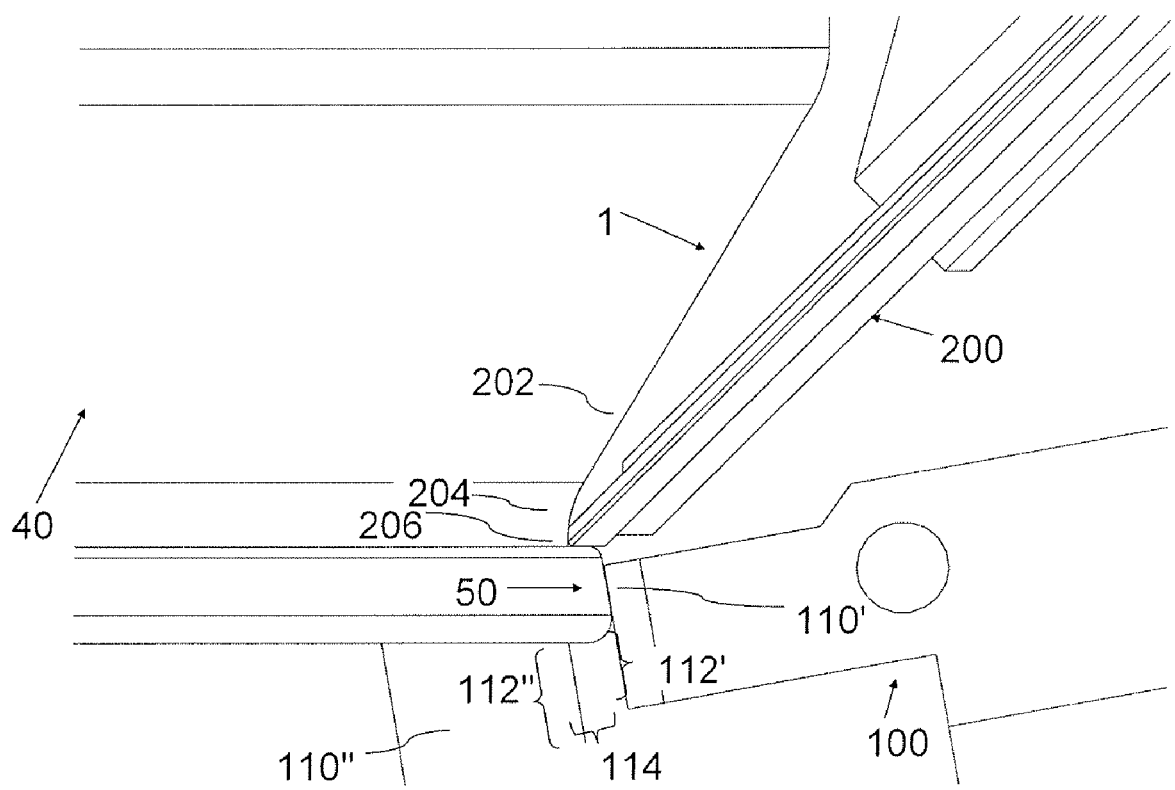
Figure 10A:
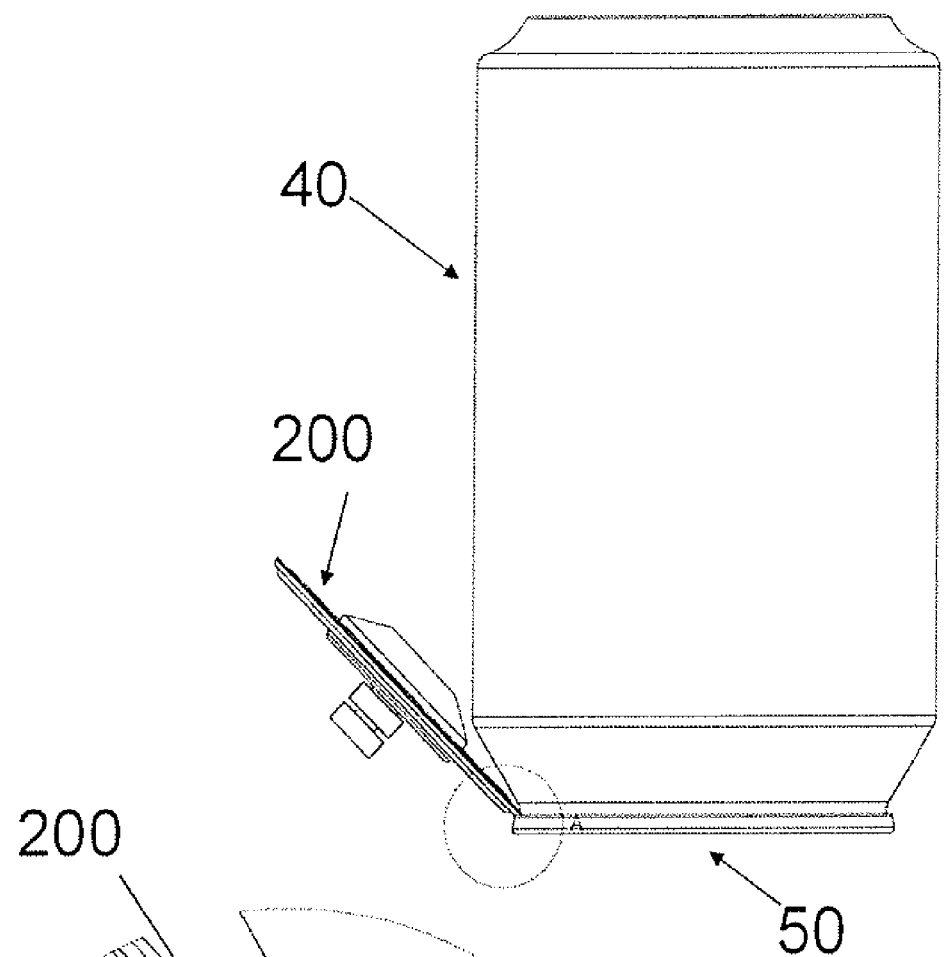
Figure 10B:
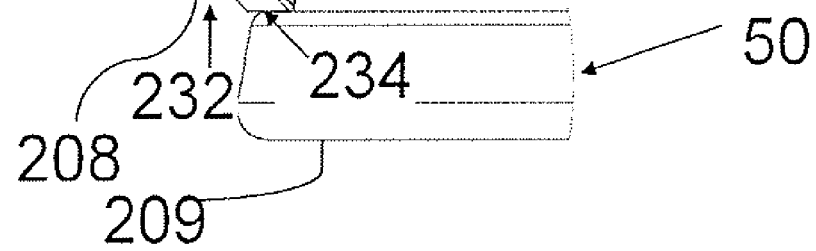
Figure 11:
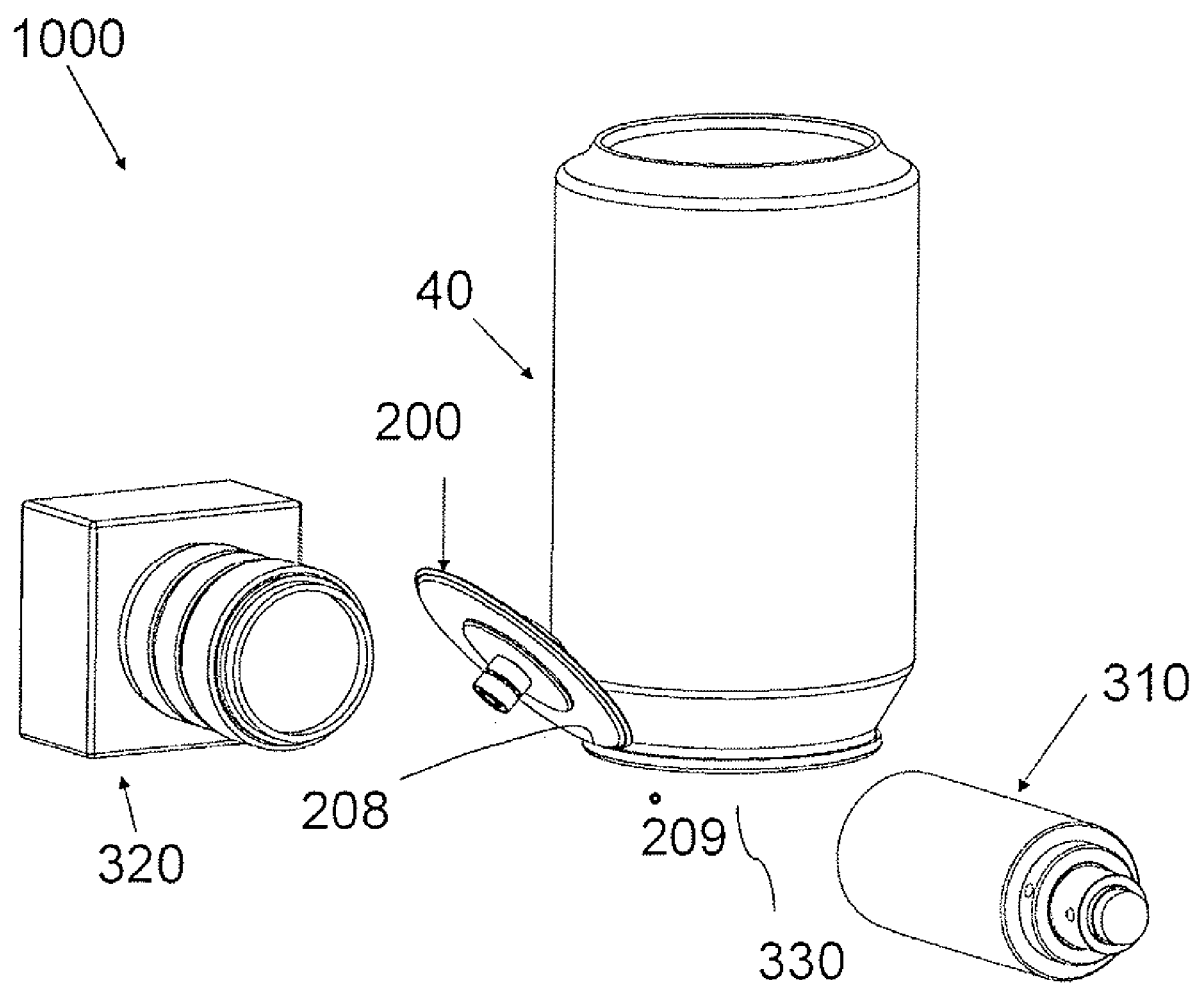
Figure 12:
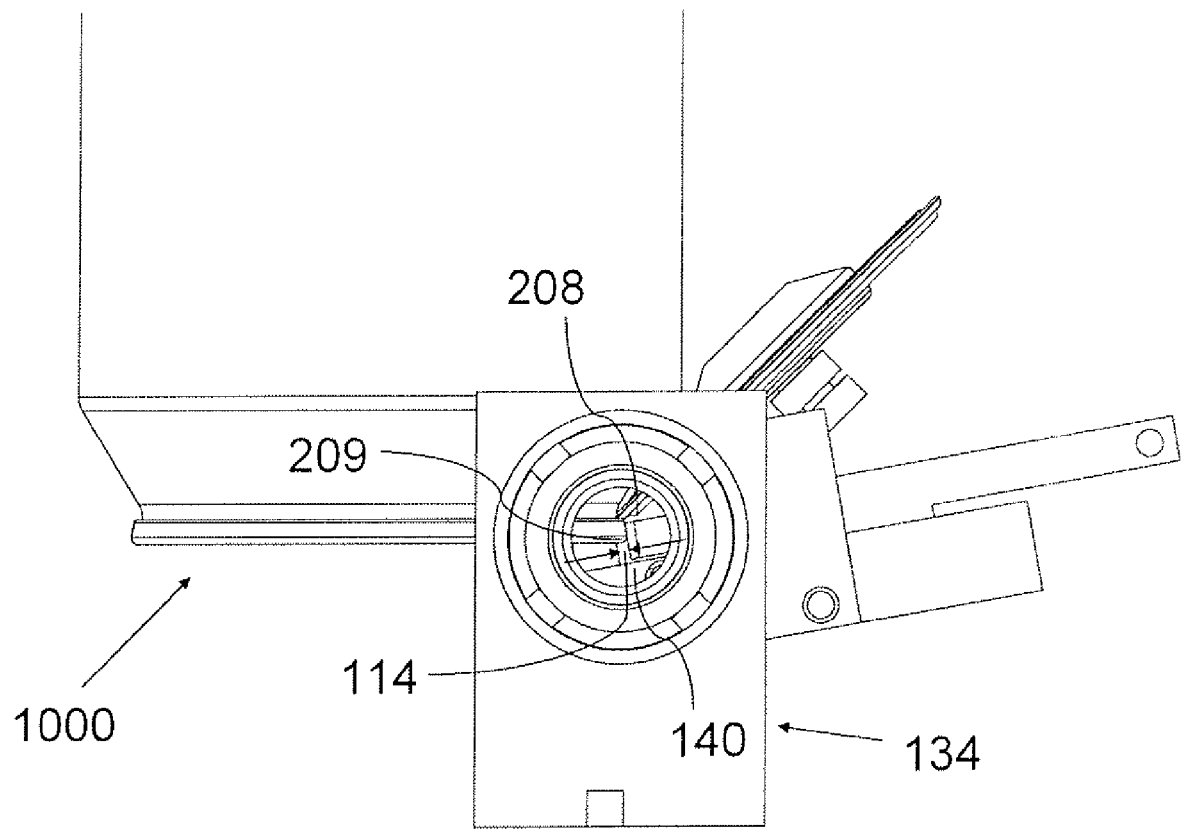

FIG. 7 presents a perspective view of a seam measurement system including a rocker for measurement of seam thickness and a length plate for measurement of seam length, together with a can positioned for measurement;

FIG. 8 depicts an expanded view of a cross section of a system like the one shown in FIG. 7, together with a cross section of a can portion;

FIG. 9 shows an expanded view of part of the system shown in FIG. 7;

FIG. 10a shows a side view of a length plate placed on the top of a can double seam;

FIG. 10b shows an expanded view of the area marked with a circle in FIG. 10a;

FIG. 11 illustrates in a perspective view a system for measurement of the length of a can seam, the system including an optical setup for optical measurement of the seam, and FIG. 12 shows in side view through an aperture area of a stationary part of a rocker the measurement area.

DESCRIPTION OF THE PREFERRED EMBODIMENTS

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The terms "comprises", "comprising", "includes", "including", and "having" together with their conjugates mean "including but not limited to".

The term "consisting of" has the same meaning as "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention.

Certain features described in the context of various embodiments are not to be considered essential features of those embodiments, unless the embodiment is inoperative without those elements.

In discussion of the various figures described herein below, like numbers refer to like parts. The drawings are generally not to scale. For clarity, non-essential elements were omitted from some of the drawing.

Figure 1A:
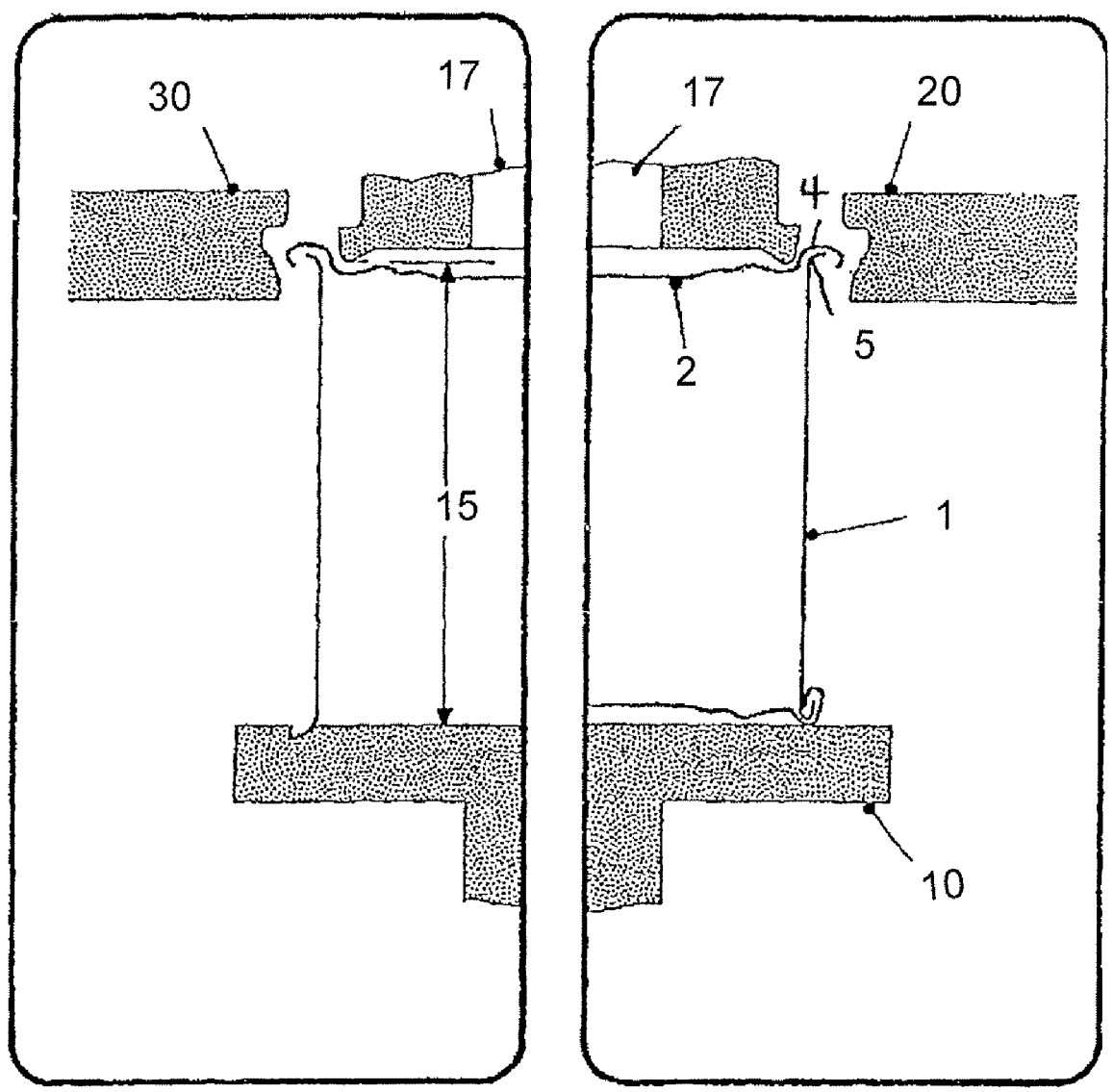

FIG. 1a shows a basic seamer prior art design for rolling either a top or a bottom end onto a can body so as to form a hermetically sealed seam. A can body 1 and an end 2 are at first forming stage clamped together by a load applied vertically to the lifter 10 against chuck 17. A first seaming roll 20, the end seaming panel 4 and can body flange 5 are rolled together and interlocked. At a second forming stage, a second roll 30 finishes the double seaming operation by tightening the seam.

Figure 1B:
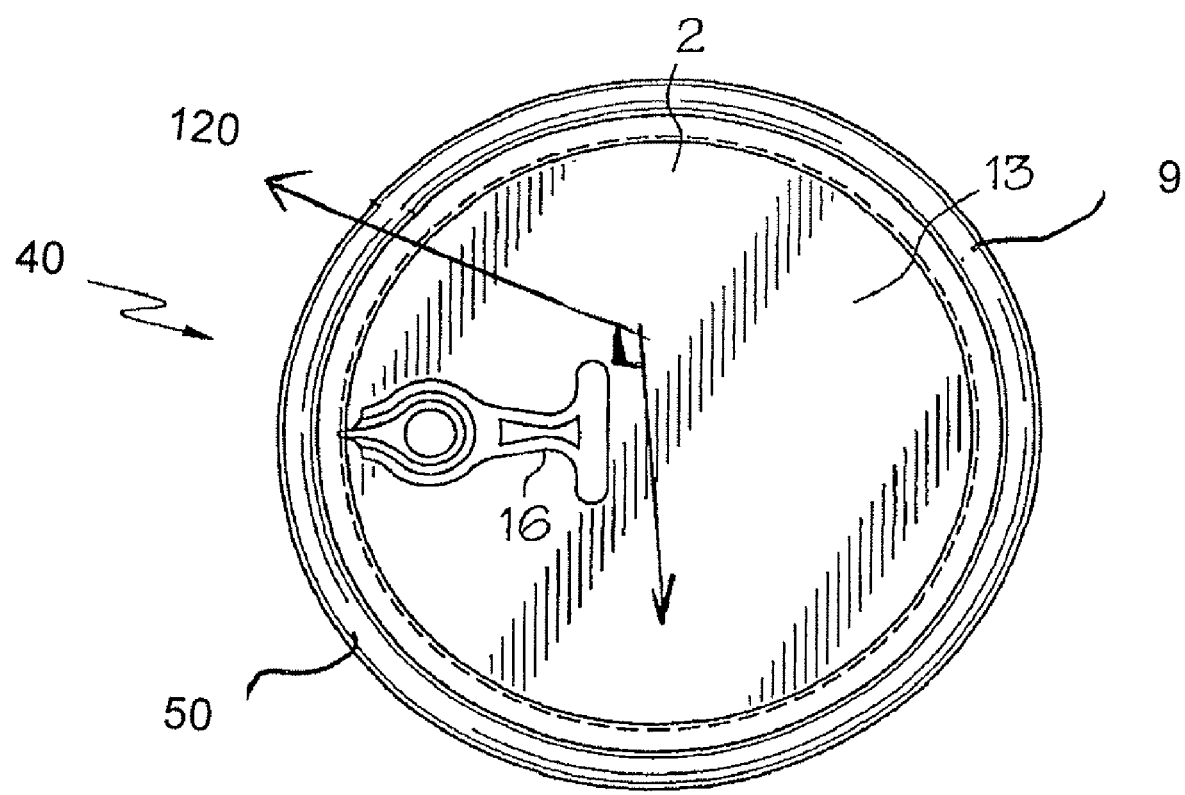

FIG. 1b illustrates a typical end of a prior art double-seamed can, formed by process and equipment similar to that described above. Seam 50 connects the end 2 to the body (not shown). The end has an essentially flat panel 13, and a chuck wall 9" between the panel 13 and the seam 50. The chuck wall 9" is typically slanted at between 1° and 8° relative to an axis 120 perpendicular to the panel 13.

Figure 2:
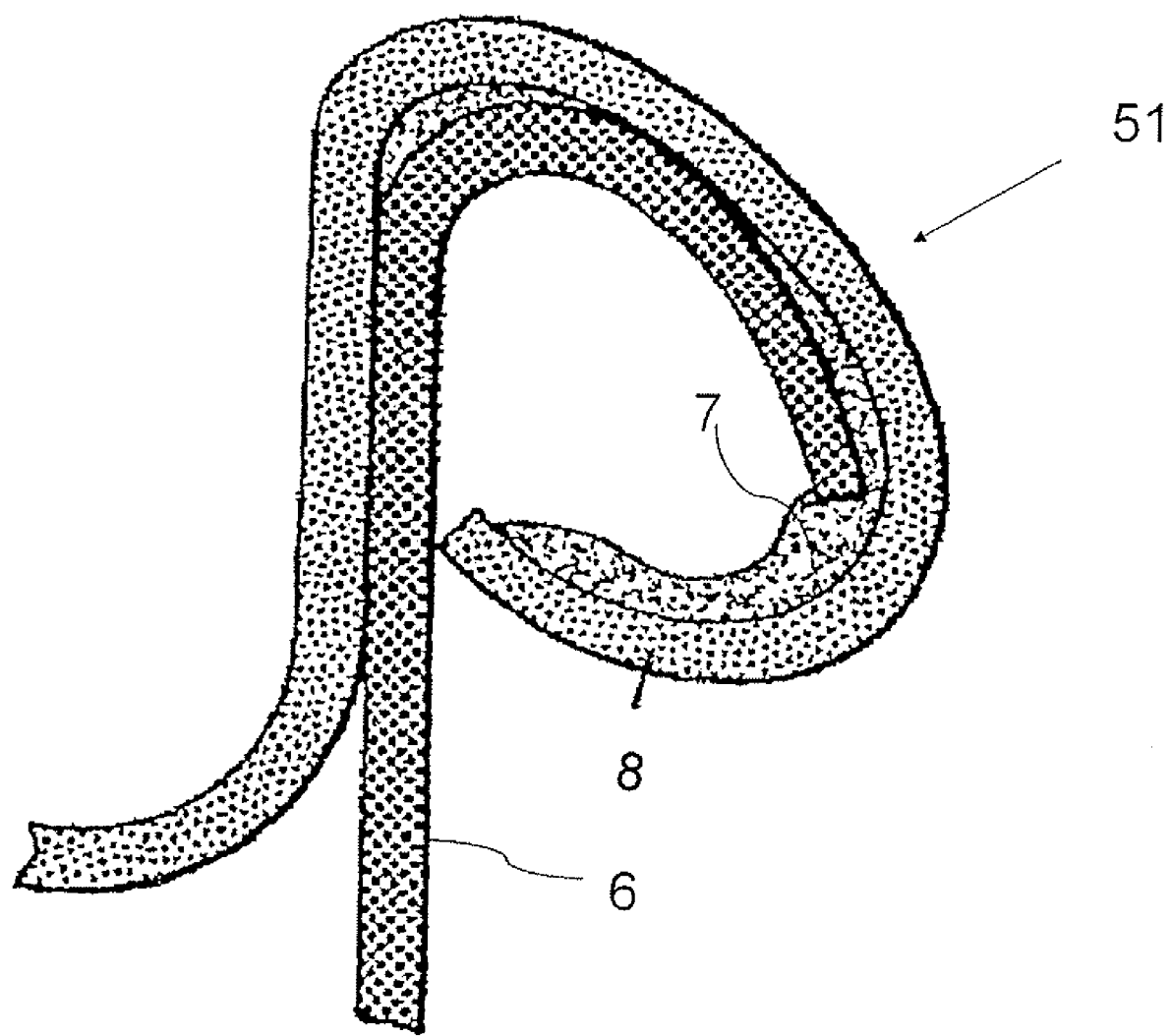
Figure 3:
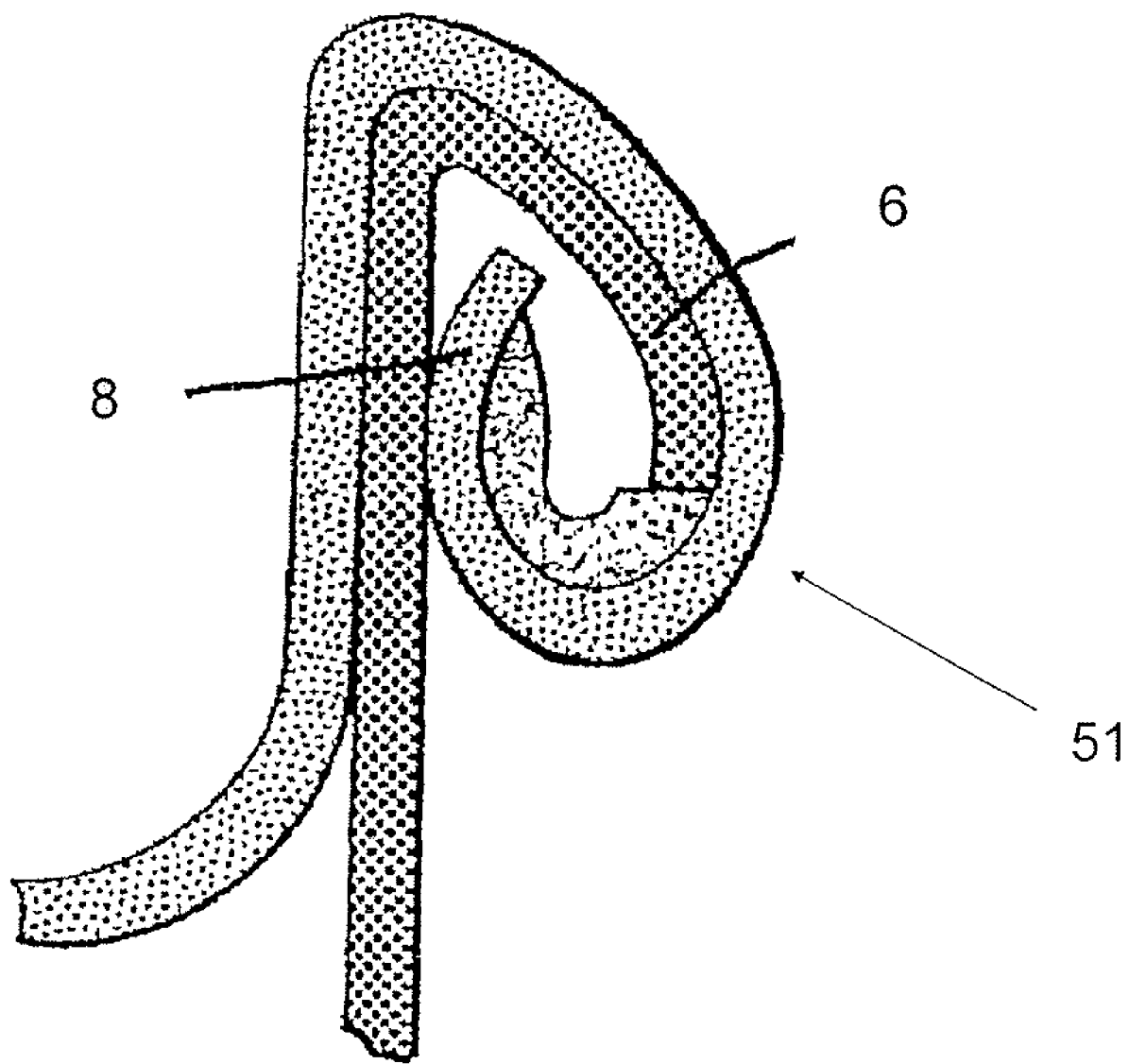

FIG. 2 shows a side section of a seam 51 after first operation. The seam 51 includes a body hook 6 embedded in a sealing compound 7, and an end hook 8. The seam 51 may be too loose, as shown in FIG. 2, for example. This could result in a short end hook 8, excessive seam length or end hook pleats. If the seam 51 is at first forming too tight, as in FIG. 3, the seam could be out of specification due to short body hook 6, long end hook 8, or insufficient seam length.

Figure 4:
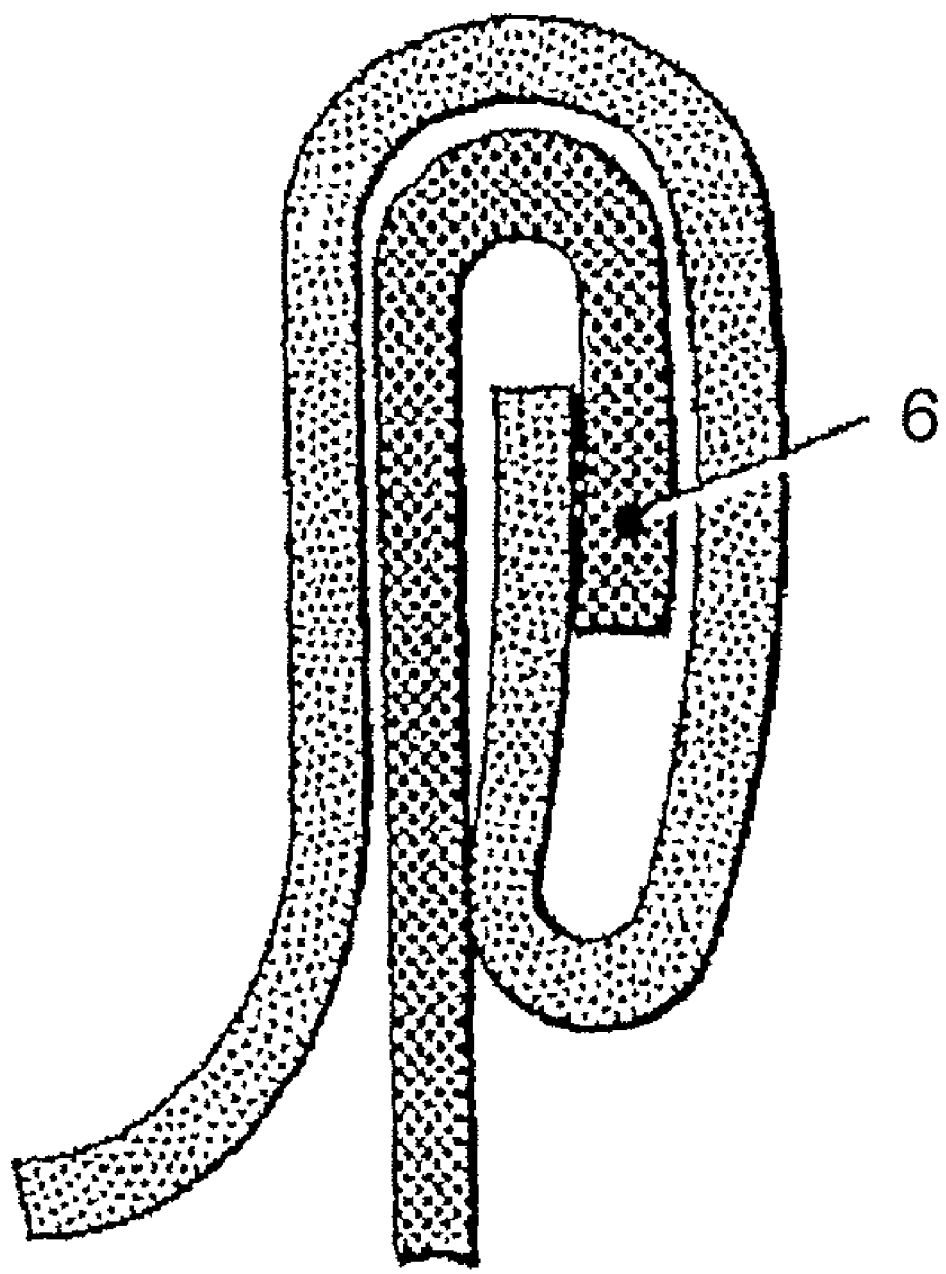
Figure 5:
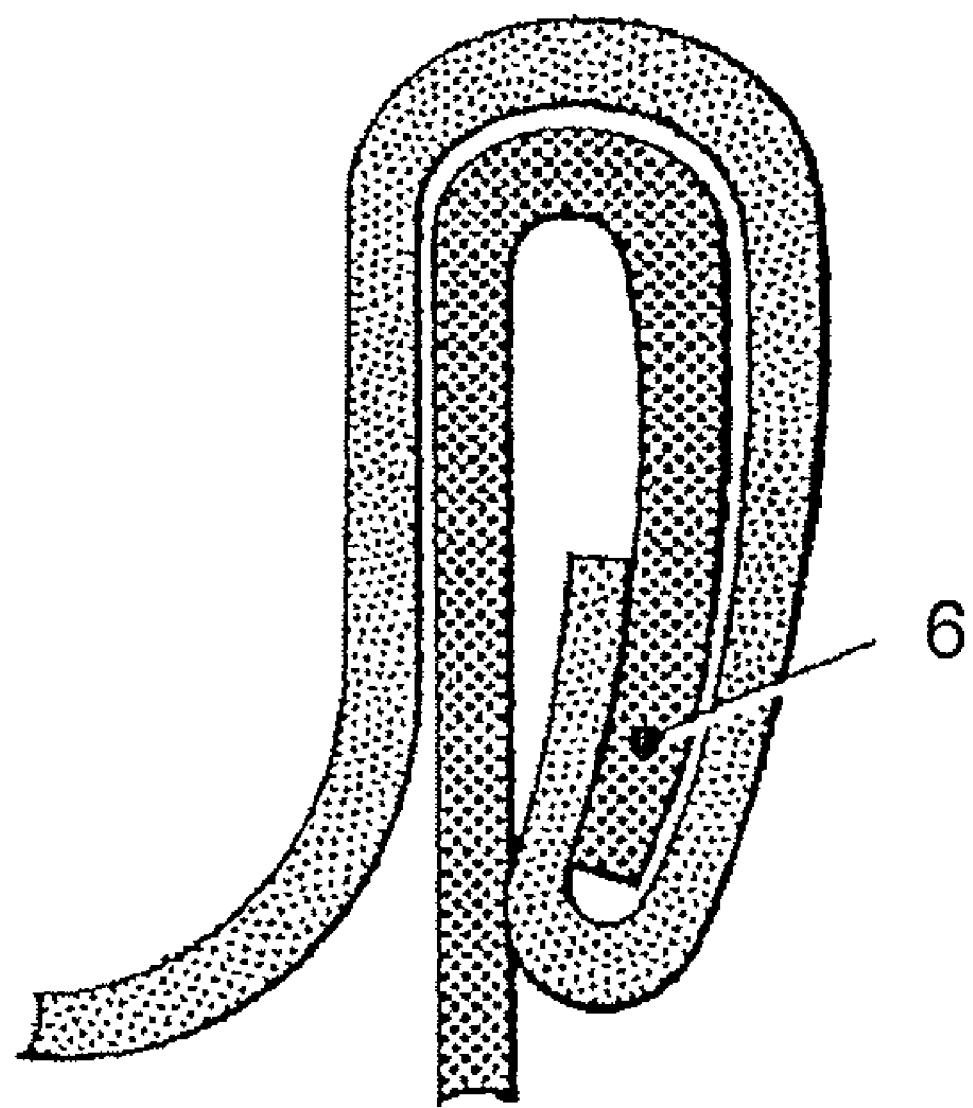
Figure 6:
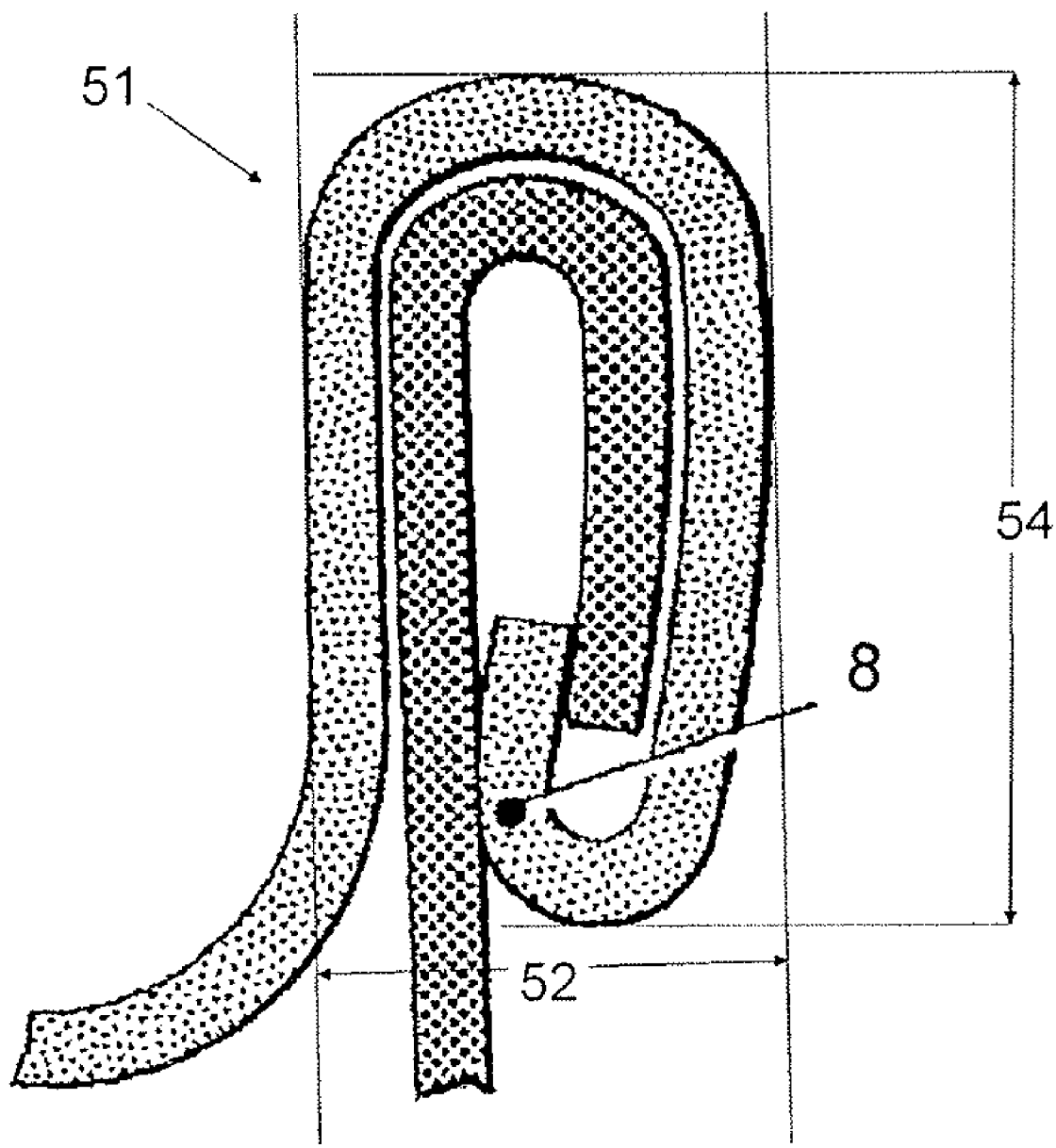

FIGS. 4 to 6 (in which sealing compound 7 has been omitted for clarity) exhibit various faults which may arise during the second forming stage. For example, the body hook 6 of FIG. 4 is too short and that of FIG. 5 is too long. The end hook 8 of FIG. 6 is too short.

FIG. 7 illustrates a perspective view of a system 1000 for measuring seam wall thickness, with some components of the system removed for clarity. FIG. 8 shows an enlarged cross section of part of the system 1000, and FIG. 9 presents a side view of part of the system 1000. The seam 50 has a chuck wall part 9", a side wall 9' essentially opposite to the seam chuck wall part 9", a seam top 9'" and a seam bottom 9"". According to one aspect, measurement of double seam thickness is performed by using two cylindrical pins, outer pin 110' and inner pin 110" (see FIGS. 8, 9) that are held by pin holders 109', 109" respectively, residing in a balanced rocker 100. The can 40 is placed on a table with a sliding top (not shown), with the end panel of the can facing the table top. Slight pressure of the outer pin 110', on the side wall 9', together with the sliding of the table top, force the chuck wall part 9" on the inner pin 110" causing a rocking movement of the pins that settles the inner pin 110" flush with the chuck wall part 9" such that the inner pin 110" is disposed at chuck wall angle 52, defined as the angle between the axis 120 perpendicular to the end panel and the chuck wall 9". The outer pin 110' is made to be essentially parallel to inner pin 110". In some embodiments the pressure will be applied by the inner pin 110" on the chuck wall part 9" causing the same results. In others, pressure will be applied by both pins.

In some embodiments, the double seam may be measured all around the can 40 by rotating the can, and in some embodiments the pins 110', 110" rotate with the can 40. In some other embodiments, either pin 110' or pin 110" rotates with the can 40. Embodiments in which neither pin 110' nor 110" will also allow performing the invention; however, such embodiments are likely to require occasional removal of sealing compound or other materials accumulated between the pins 110', 110" to maintain the most consistent accuracy in double seam thickness measurements. Removal of sealing compound may also benefit measurement in which at least one pin rotates. The can rotates using three or more contact points which rotate it while ensuring that the can remains in the same orientation with the pins 110' and 110" throughout the process. Some of these contact points can be pins 110' and or 110". Typically the can is pinned using 3 pins while one of these pins, performs the rotation. These pins can be made from any material, but typically the rotating pin is covered by high friction material which ensures traction with the can during the turning process.

The turning mechanism will typically be driven by a stepper motor, DC motor or pneumatic pressure.

The rocker 100 may be balanced for accurate seam thickness measurement by appropriately configuring the rocker 100, in particular the location of the center of mass of the rocker 100. Note that the rocker 100 need not be driven to perform the rocking during the rotation of the can 40.

In some embodiments, during the rotation, a side of the pins 110', 110" is exposed to radiation (for example Laser, parallel light, ultrasonic waves, microwaves, X-rays, radio waves, directional white light or other radiation) from a radiation source (not shown). A sensor (not shown) such as a CCD is positioned on the opposite side of the pins 110', 110", in an appropriate location where it can receive radiation passing between the pins, to detect the silhouette of the pins 110', 110". The thickness of the gap is calculated from the detected silhouette. For simplicity, the radiation hereinbelow will be referred to as "light".

Refer now to FIG. 9, depicting an expanded view of part of the apparatus shown in FIG. 8. In preferred embodiments, the pins 110', 110" are positioned relative to the seam 50 such that parts 112', 112" of each of the pins 110', 110" (respectively) extend beyond the seam 50, preferably at least below the seam 50, such that the silhouette includes a gap 114 between the pins 110', 110" which is devoid of the seam 50 at all measurement points around the circumference of the seam 50.

The rocker 100 is able to make an NDT measurement of the seam thickness at the precise chuck angle 52. By adapting to the chuck wall angle 52, more accurate and/or precise seam thickness measurements are made than are made by commercially available systems. Operators have minimal influence on the results and different chucks with different chuck angles will work without any modifications. The operators are merely required to insert the can 40 into position, and activate the rocker 100, or the rocker 100 automatically works and continually adapts the pins 110', 110" to the chuck wall angle 52 upon insertion of the can and throughout the rotation of the can 40.

The selected radiation may have some bearing on the accuracy of the system 1000, as do the selected radiation sources (more accurate), and the optics and sensor qualities. Higher quality of production of seam also allows more accurate measurement of the seam thickness.

In various embodiments, the pins 110', 110" may be created in different sizes.

The rocker 100 may be integrated with signal and data collection and processing means, data storage and results presentation means that allow presentation of the results of thickness measurement all along the circumference of the seam 50. The thickness results of measurements at points along the circumference may be presented in a graphical form, e.g. thickness vs. position along the can (with an arbitrary zero point at the first measurement), in the form of thickness-position points. A line may interpolate between adjacent measurements points to provide a continuous measurement line along the circumference.

The rocker 100 may be part of a measurement system, in some laboratory embodiments tests may be performed one can at a time in a lab environment. In other embodiments, the system grabs a number of cans off the production line every settable number of minutes, tests them, and alerts when a problem is detected with a certain threshold of points either with seam length, seam thickness. Problems can include values going out of tolerance, range going out of tolerance or patterns interacting between length/thickness which can indicate a problem.

In some embodiments, a manual mode of operating the system is available—cans are brought to the machine, lined up and the test is then started—the system may produce a report and statistics graphs at the end of the measurement process. In some embodiments, an automatic mode is available—the system grabs one can from each head every X minutes and tests all of the grabbed cans. If for example one of the cans is marked by a dimple, a sign, a barcode, or any other technique as being from Head #1, the system will detect it and match that can with the correct head on the report.

A calibration process may be used to create the calculation values, in which pixel values are converted into actual useable measurement data, which can be used by the system operators. The system can utilize an optical or mechanical instrument, of known size, which allows the software to calculate the pixel dimensions. Additionally, when optics might have deformation, the calibration process can utilize patterns on the calibration gauge image to detect the lens deformation and compensate these so that the image received will have been lens compensated and remains linear. An operator will therefore place a calibration gauge as a can, type the values as supplied by the calibration gauge manufacturer, at which time the software will detect the conversion between pixel width and height against which will result in the detected value being the same as the calibration gauge's stated value.

The systems may detect and locate hard to find errors that can be easily missed in commercially available seam tests and systems, errors such as compound buildups, variations around the seam, skids, wrinkle, and more. The system will stop at a point that can be correlated against in the graphs—such that the scan will always end with the can resting at angle 0. That way, an operator can take the can and put it against a circular (spider/spider-web) graph and determine where the defect point is on the screen and on the actual can. To enable this, the software will likely add a small extra amount of rotation and instead of rotating 360 degrees, will rotate up to 120 degrees more to ensure that the first part of the measurement correlates well with the last part as the measurement is performed in a circle. When the can rotation stopped, the software will declare this as angle 360 (or point zero) for easy identification.

The system may provide a simple and safe alternative to X-ray based systems.

The NDT system has the potential of being faster, repeatable and able to detect issues that conventional external seam gauges cannot.

Referring again to FIGS. 7-9, according to another aspect, a circular length plate 200 is provided, that can enable measuring the seam height 54 (shown in FIG. 6). After appropriately positioning (similar to any of the procedures described above) a can 40 for measurement, the length plate 200 is moved toward a wall 202 of the can body 1, and after contacting the wall 202 the length plate 200 moves down in a way that it finds the neck 204 of the can and then further moves down so as to find the point 206 where the seam 50 touches the neck 204. The length plate 200 then resides on the top 9′′′ of the seam 50, at that niche point 206.

FIG. 10*a* shows a side-view of the length plate 200 in position for measurement against can 40.

FIG. 10*b* shows an expanded view of the area marked with a circle in FIG. 10*a*.

The height 54 can be calculated based on the optical measurement of the distance between two points, one point 208 on the length plate 200, and the other a reference point 209.

As the can 40 (and the bottom 9′′′′ of seam 50) resides during the measurement on a table or other surface, the reference point 209 is at constant height during the rotation of the can, and thus may conveniently be related to the height of such surface, as shown for example in FIG. 10*b*.

As shown in a perspective view in FIG. 11, the length plate 200, in particular the point 208, as well as reference point 209, is exposed to light from a light source 310 on one side of the length plate 200. A sensor 320 such as a CCD is positioned on the opposite side of the length plate 200, in an appropriate location where it can receive partially blocked light. The distance between the points 208, 209 is calculated from the detected silhouette. Note that the measured distance between the points 208 and 209 (depending upon where the reference point is) is not necessarily equal to the actual height of the seam 50 at the measuring point. However, if said distance is not equal, then in some embodiments, the real height of the seam may be estimated from the measured distance, by knowing the vertical distance between tooth 232 (which includes point 208) and edge 234 that actually contacts the seam 50 (see FIG. 10*b*).

The reference point 209 may be directly optically measured, or its position may be assumed to be at a position determined before measurement commences, for example a point on the table.

The following measuring options are thus available for measuring seam height:
 (i) Measuring a point on edge 234, not necessarily requiring a length plate, as the point may be measured by processing an image of the seam;
 (ii) Measuring tooth 232 and deriving from that measurement the location of point 208;
 (iii) Measuring point 209 from an image including the point, and
 (iv) Identifying and setting point 209, either arbitrarily or by way of reference to the measurement of the table.

Calculation of the seam length may be calculated by either of two methods: (a) calculation of the absolute distance between edge 234 (itself either calculated or measured), and point 209 (determined from an image or decided as a point on the table top), or (b) calculation of the vertical component of the distance 234-209 only, i.e. without considering the horizontal component of the distance.

Method (b) is preferable, since the horizontal measurement introduces more noise and is not essential for the seam length measurement.

In preferred embodiments, the length plate 200 also rotates around with the rotation of the can 40 and maintains its position on the niche 206. However, in other embodiments the length plate does not rotate while the can 40 is rotated.

As with the rocker, the length plate 200 together with means for positioning and moving the length plate 200 may be integrated with signal and data collection and processing means, data storage and results presentation means that allow presentation of the results of length measurement all along the circumference of the seam 50. The length results of measurements at points along the circumference may be presented in a graphical form, e.g. length vs. position along the can (with an arbitrary zero point at the first measurement), in the form of length-position points. A line may interpolate between adjacent measurement points to provide a continuous measurement line along the circumference. When not in use, the software can locate the seam length point automatically and utilize that measurement as if a length plate was present.

The length plate 200 may be part of a measurement system, in some laboratory embodiments tests may be performed one can at a time in a lab environment. In other embodiments, the system grabs a number of cans off the production line every settable number of minutes, tests them, and alerts when there is a problem.

In preferred embodiments, the length plate 200 also substantially conforms with at least part of the neck 204, as shown for example in FIG. 10b, thus being stably held against the can 40 during rotation of the can 40.

Referring back to FIG. 7, a seam measuring system 1000 including the rocker 100 and the length plate 200 is shown.

Note that the rocker pins 110', 110" and the length plate 200 are positioned so that they contact the seam at the same point, i.e. along a line that would be formed from vertically cutting the seam, as in FIG. 8.

Furthermore, as shown in FIG. 9, the geometries of the length plate 200 (and the parts controlling its movement) and the rocker 100 are designed to leave adequate space between them and the can 40, except at the intended contact points, to prevent undesirable contact between each other, as well as the table holding the can 40. In addition, their geometries are such as to leave adequate space between each other and them and the light source and light sensor, for accurate measurement of silhouettes.

When in focus, the system will be able to distinguish between light and dark by utilizing a threshold algorithm. This algorithm allows detection of the various components, including the pins, table and length plate. Detection algorithms locate the correct angle and position of each component on the image. Thickness measurement comprises the geometric distance between the seam thickness pins, or their likeness on the image. The seam length comprises the seam length point as it correlates to the seam thickness. These pixel positions are converted mathematically, by means of compensating for lens deformation and linear conversion factors, into their distance counterparts, based on the information gathered during the calibration process. For example, if a pixel's width is determined during the calibration process to be 10 microns, if a particular distance is found to be 10 pixels wide, the software will be able to extrapolate that this width is actually 100 microns in the real world. Compensation for defocusing and lens deformation may require slight modifications to this value based on the position of the lines on the image.

Referring again to FIG. 7, the rocker 100 swivels on the stationary part 134.

Now referring to the setup in a system embodiment 1000 shown in FIGS. 7 and 11, in which the optical means are configured to allow measurement of both seal thickness and seal length, stationary part 134 coincides with an light beam 330 from a light source 310, aimed at the area of the measurement of the thickness and height, e.g. points 208, 209, and pin parts 112' and 112" in FIGS. 9, 10b. In order to allow the light beam through the stationary part 134, the stationary part has an aperture 140 in the appropriate place. The aperture 140 may include a lens for focusing or defocusing the light to make its flux area near the seam similar to the size of the area of the measurement of the thickness and height and produce the desired silhouette.

FIG. 12 shows the system 1000 from a side view, showing through the aperture 140 the points 208, 209 and the gap 114 between the pins.

Point 208 leaves adequate space from rocker 100, and can 40, to allow accurate optical measurement of the double seam height. Preferably the space is also adequate for leaving clearance from the can that is sufficient to prevent optical interference or obstruction from sealing compound protruding from the double seam. Nevertheless, it may be preferable to occasionally remove sealing compound accumulated in the space.

In other embodiments, other optical (or other radiation) setups may be used. For example, the light may follow an indirect path from the light source to the measurement area by adding mirrors to the optical setup, and placing the mirrors and directing the light so that the light bypasses the stationary part 134. In other embodiments, the stationary part 134 may seat the rocker 100 yet be geometrically shaped (e.g. hemisphere) and positioned to allow the light from the light beam 330 to pass from the light source 310 to the double seam 50 without obstruction by the stationary part 134 (not shown).

The scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

What is claimed is:

1. A system for measurement of a can seam of a can comprising an end panel, the end panel comprising the seam, the seam comprising a circumference, a seam top, a seam bottom, a seam chuck wall part and an opposite seam wall essentially opposite the seam chuck wall part, the system comprising:
   a table comprising a table top;
   a rocker comprising an inner pin and an outer pin essentially parallel to each other, the rocker configured to allow, when the end panel of the can is facing the table top, slight pressure of the outer pin on the opposite wall forcing the chuck wall part on the inner pin, and/or slight pressure of the inner pin on the chuck wall part forcing the opposite wall on the outer pin, causing rocking movement of the pins, that settles the inner pin flush with the chuck wall part, and/or the outer pin flush with the opposite wall, respectively, such that the inner pin and outer pin are disposed at chuck wall angle;
   means for rotating the can, allowing the inner pin to settle flush with the chuck wall part, and the outer pin to settle on a peak point on the opposite wall, at measurement points on the circumference of the seam; and
   measuring means configured to be able to measure a gap between the inner pin and the outer pin at the measurement points.

2. A system for measurement of a can seam, the seam comprising a circumference, a seam top, a seam bottom, a seam chuck wall part and an opposite seam wall essentially opposite the seam chuck wall part, the system comprising:
   a length plate having an edge;
   positioning means configured to allow positioning a can for measurement of the distance between the seam top and seam bottom;
   means for moving the length plate until the length plate edge resides on the seam top;
   measurement means configured to allow measuring a plate distance between a point on the length plate and a fixed reference point; and
   the distance representing a seam distance between the seam top and the seam bottom.

3. A system for measurement of a can seam, the seam comprising a circumference, a seam top, a seam bottom, a seam chuck wall part and an opposite seam wall essentially opposite the seam chuck wall part, the system comprising:
   a length plate comprising an edge;
   means for moving the length plate until the length plate edge resides on the seam top;
   means configured to allow measuring a plate distance between a point on the length plate and a fixed reference point, the distance representing a seam distance between the seam top and the seam bottom;

a rocker comprising an inner pin and an outer pin essentially parallel to each other, the rocker configured to allow applying slight pressure of the inner pin on the chuck wall part and slight pressure of the outer pin on the opposite wall, and rocking movement of the outer and inner pin relative to the seam, thereby forcing the inner pin to settle flush with the chuck wall part, and the outer pin to settle on a peak point on the side wall; and means for rotating the can, allowing the inner pin to settle flush with the chuck wall part, the outer pin to settle on a peak point on the side wall at measurement points on the circumference of the seam, and the reference point to be at essentially constant height during the rotation of the can; and measuring means configured to allow measuring both a plate distance between a point on the length plate and a reference point, and a distance representing a seam distance between the seam top and the seam bottom.

4. The system of claim 1, wherein at least one pin is configured to rotate with the can.

5. The system of claim 2, wherein the length plate is circular and configured to rotate with the can.

6. The system of claim 2, further comprising means for rotating the can, allowing the reference point to be at constant height during the rotation of the can.

7. The system of claim 2, the length plate comprising a tooth, essentially parallel to the edge, wherein a point on the tooth is selectable for measuring a distance between the tooth and the reference point representing a distance between the seam top and the seam bottom.

8. The system of claim 2, wherein measurement means comprises an optic setup, the optic setup comprising a light source capable of emitting light and a sensor of the light, wherein the sensor is positioned to receive light partially blocked by the pins to detect a silhouette of the pins, such that the silhouette comprises a gap between the pins representing a distance between the seam chuck wall part and the opposite seam wall.

9. The system of claim 8, wherein the settled pins are positioned relative to the seam such that parts of each of the pins extend beyond the seam, such that the gap is devoid of the seam.

10. The system of claim 2, wherein measurement means comprises an optic setup, the optic setup comprising a light source capable of emitting light and a sensor of the light, wherein the sensor is positioned to receive light partially blocked by the length plate to detect a silhouette of the length plate, such that the silhouette comprises a gap between the length plate and the reference point.

11. The system of claim 7, wherein measurement means comprises an optic setup, the optic setup comprising a light source capable of emitting light and a sensor of the light, wherein the sensor is positioned to receive light partially blocked by the length plate to detect a silhouette of the length plate, such that the silhouette comprises a gap between a point on the tooth and the reference point.

12. The system of claim 3, wherein measurement means comprises an optic setup, the optic setup comprising a light source capable of emitting light and a sensor of the light, wherein the sensor is positioned to receive light partially blocked by both the length plate and the pins, to detect a silhouette of the length plate and the pins, such that the silhouette comprises a gap between the length plate and the reference point and a gap between the pins representing a distance between the seam chuck wall part and the opposite seam wall.

13. The system of claim 12, wherein the rocker swivels on a stationary part, the stationary part comprising an aperture allowing light from the light source to be aimed throughout the stationary part at the pins and length plate.

14. The system of claim 13, the aperture comprising a lens for focusing or defocusing the light passing through the aperture.

15. The system of claim 1, further comprising signal processing means configured to process signals received by the sensor into data, means for storing the data and means for presenting the data.

16. The system of claim 2, the can comprising a neck, wherein the length plate substantially conforms to at least part of the neck, thereby allowing the plate to be stably held against the can during rotation of the can.

17. The system of claim 1, wherein the table top is a sliding table top.

18. The system of claim 2, wherein the length plate comprises at least one tooth, wherein the point on the length plate is a point on a tooth, the point is known before measuring.

19. The system of claim 4, wherein at least one rotating pin is covered by high friction material ensuring traction with the can during the rotation.

20. The system of claim 3, wherein at least one pin is configured to rotate with the can.

21. The system of claim 3, wherein the length plate is circular and configured to rotate with the can.

22. The system of claim 3, further comprising means for rotating the can, allowing the reference point to be at constant height during the rotation of the can.

23. The system of claim 3, the length plate comprising a tooth, essentially parallel to the edge, wherein a point on the tooth is selectable for measuring a distance between the tooth and the reference point representing a distance between the seam top and the seam bottom.

24. The system of claim 3, wherein measurement means comprises an optic setup, the optic setup comprising a light source capable of emitting light and a sensor of the light, wherein the sensor is positioned to receive light partially blocked by the pins to detect a silhouette of the pins, such that the silhouette comprises a gap between the pins representing a distance between the seam chuck wall part and the opposite seam wall.

25. The system of claim 3, wherein measurement means comprises an optic setup, the optic setup comprising a light source capable of emitting light and a sensor of the light, wherein the sensor is positioned to receive light partially blocked by the length plate to detect a silhouette of the length plate, such that the silhouette comprises a gap between the length plate and the reference point.

26. The system of claim 3, further comprising signal processing means configured to process signals received by the sensor into data, means for storing the data and means for presenting the data.

27. The system of claim 3, the can comprising a neck, wherein the length plate substantially conforms to at least part of the neck, thereby allowing the plate to be stably held against the can during rotation of the can.

28. The system of claim 3, wherein the table top is a sliding table top.

29. The system of claim 3, wherein the length plate comprises at least one tooth, wherein the point on the length plate is a point on a tooth, the point is known before measuring.

30. The system of claim 2, further comprising signal processing means configured to process signals received by the sensor into data, means for storing the data and means for presenting the data.

* * * * *